United States Patent
Wang et al.

(10) Patent No.: US 9,421,359 B2
(45) Date of Patent: Aug. 23, 2016

(54) PROBE FOR IMPLANTABLE ELECTRO-STIMULATION DEVICE

(75) Inventors: Ke Wang, Eindhoven (NL); Hubert Cecile Francois Martens, Eindhoven (NL); Franciscus Paulus Maria Budzelaar, Eindhoven (NL); Dirk Willem Harberts, Eindhoven (NL); Michael Marcel Jose Decre, Eindhoven (NL); Jeroen Jacob Arnold Tol, Eindhoven (NL)

(73) Assignee: MEDTRONIC BAKKEN RESEARCH CENTER B.V., Maastricht (NL)

( * ) Notice: Subject to any disclaimer, the term of this patent is extended or adjusted under 35 U.S.C. 154(b) by 725 days.

(21) Appl. No.: 13/120,758

(22) PCT Filed: Oct. 7, 2009

(86) PCT No.: PCT/IB2009/054395
§ 371 (c)(1),
(2), (4) Date: Mar. 24, 2011

(87) PCT Pub. No.: WO2010/044015
PCT Pub. Date: Apr. 22, 2010

(65) Prior Publication Data
US 2011/0184495 A1    Jul. 28, 2011

(30) Foreign Application Priority Data
Oct. 15, 2008   (EP) .................................... 08166665

(51) Int. Cl.
*A61N 1/05*   (2006.01)
*H05K 9/00*   (2006.01)
*A61N 1/08*   (2006.01)

(52) U.S. Cl.
CPC *A61N 1/05* (2013.01); *H05K 9/002* (2013.01); *A61N 1/056* (2013.01); *A61N 1/0529* (2013.01); *A61N 1/0531* (2013.01); *A61N 1/0551* (2013.01); *A61N 2001/086* (2013.01)

(58) Field of Classification Search
CPC . A61N 1/0529; A61N 1/0531; A61N 1/0534; A61N 1/0551; A61N 1/0556; A61N 1/05; A61N 1/056; A61N 2001/086; A61B 5/04001; A61B 5/04005; A61B 5/04007; A61B 5/04008; H05K 9/002
USPC ........................... 600/377, 378; 607/116, 117
See application file for complete search history.

(56) References Cited

U.S. PATENT DOCUMENTS 7,120,502 B2 * 10/2006 Tuominen ..................... 607/119
7,509,175 B2 *  3/2009 Sparks et al. ................. 607/133

(Continued)

FOREIGN PATENT DOCUMENTS

| WO | 2007047966 A2 | 4/2007 |
| WO | 2008018067 A2 | 2/2008 |
| WO | 2008095059 A1 | 8/2008 |

OTHER PUBLICATIONS

Chinese Office Action dated Jun. 3, 2013 for Chinese patent application No. 200980140999.7.

(Continued)

*Primary Examiner* — Amanda Patton
(74) *Attorney, Agent, or Firm* — Shumaker & Sieffert, P.A.

(57) ABSTRACT

The invention relates to a probe for an implantable electro-stimulation device. The probe (20) has a distal end (12) and a proximal end (13), and moreover comprises: one or more electrodes (11) a shield (21) of conducting material covering a major part of the probe, said shield extending from the vicinity of at least one of the one or more electrodes (11) towards the proximal end (13) or towards the distal end (12) of the probe (20); and a layer (22a, 22b) of insulating material covering part of the shield (21) in the vicinity of the at least one of the one or more electrodes. The shield protects wires (14), extending from electrodes to the proximal end of the probe, from undesired interference of external RF fields. The exposed part of the shield not covered by the layer of insulating material serves as a return electrode for the electrostimulation signal path.

24 Claims, 5 Drawing Sheets

(56) References Cited

U.S. PATENT DOCUMENTS

| | | |
|---|---|---|
| 8,275,464 B2* | 9/2012 | Li et al. .................. 607/63 |
| 2002/0022866 A1 | 2/2002 | Borkan |
| 2003/0144719 A1 | 7/2003 | Zeijlemaker |
| 2003/0163178 A1* | 8/2003 | Davison et al. .......... 607/101 |
| 2006/0247747 A1* | 11/2006 | Olsen ............ A61N 1/0529 607/116 |
| 2007/0060955 A1* | 3/2007 | Strother et al. ............ 607/2 |
| 2007/0100408 A1 | 5/2007 | Gerber |
| 2009/0149933 A1 | 6/2009 | Ameri |
| 2013/0046292 A1* | 2/2013 | Janssen et al. ............ 606/14 |

OTHER PUBLICATIONS

Office Action dated Feb. 17, 2014 for Chinese Patent Application No. 200980140999.7.

International Preliminary Report on Patentability from Counterpart International Patent Application No. PCT/IB2009/054395, dated Apr. 19, 2011, 7 pp.

International Search Report and Written Opinion from Counterpart International Patent Application No. PCT/IB2009/054395, dated Mar. 12, 2009, 9 pp.

\* cited by examiner

ABSTRACT?

PROBE FOR IMPLANTABLE ELECTRO-STIMULATION DEVICE

FIELD OF THE INVENTION

The present invention relates to a probe for an implantable electro-stimulation device.

BACKGROUND OF THE INVENTION

Implantable electro-stimulation devices are commonly used today to treat patients suffering from various ailments. After implant of an implantable device for electric stimulation, such as pacemakers or Deep Brain Stimulation (DBS) devices, the device may cause heating of the device and surrounding tissue, either at the normal use of the implantable device or during scanning of the patient and device by e.g. Magnetic Resonance (MR) scanning.

The human tissue, in particular brain tissue, is sensitive to temperature raises; the maximum allowed temperature increase of brain tissue is 1° C. in that further temperature increases may have profound, negative effects on single neuron and neuronal network function. Therefore it is of concern to minimize heating effects at and around an implanted electro-stimulation device as well as to prevent undesired stimulation of the human tissue due to induced currents near the electro-stimulation device during MR scanning.

Moreover, safety and compatibility during MR scanning is of great concern for implantable electrical stimulation devices; in particular, shielding from external electromagnetic fields is important in order to avoid undesired interference of the external electromagnetic fields, e.g. RF signals. Optimum shielding effect requires the shield to be as close as possible to the electrode/electrodes of the implantable electro-stimulation device.

Furthermore, it is of concern to provide a probe for electro-stimulation wherein the stimulation is focused mainly at a region of interest and is preferably effective only at the region of interest. In order to reduce power consumption and thereby increase battery life time, a return electrode may be incorporated in the implantable electro-stimulation device in order to reduce the circuit impedance and/or provide a well defined current return path. Such a return electrode should be situated at a certain minimum distance from the electrode/electrodes of the probe in order to prevent the shunting of stimulation currents directly to the return electrode which would diminish the volume of tissue that could be excited by the stimulation currents.

WO 2008/018067 discloses a neural stimulation system using various electrode configurations and/or anodic flow to control the stimulation effect. In some embodiments, a remote cathodal collecting electrode is used. In some embodiments, a multi-polar stimulation includes anodes on either side of a cathode. WO 2008/018067 does not relate to the shielding of the system for neural stimulation against external electromagnetic fields.

Hence, an improved implantable electro-stimulation device comprising a probe with one or more electrodes would be advantageous, and in particular an electro-stimulation device with increased battery life time and/or a probe with improved shielding against external electromagnetic fields, such as RF signals, would be advantageous.

SUMMARY OF THE INVENTION

Accordingly, the invention preferably seeks to mitigate, alleviate or eliminate one or more of the above mentioned disadvantages singly or in any combination. In particular, it may be seen as an object of the present invention to provide an implantable electro-stimulation device that reaches the above mentioned objectives with regard to battery life time, focused electro-stimulation and safety with regard to external fields.

This object and several other objects are obtained in a first aspect of the invention by providing probe for an implantable electro-stimulation device, said probe having a distal end and a proximal end, said probe moreover comprising: one or more electrodes; a shield of conducting material covering a major part of the probe, said shield extending from the vicinity of at least one of the one or more electrodes towards the proximal end or towards the distal end of the probe; and a layer of insulating material covering part of the shield in the vicinity of at least one of the one or more electrodes.

The shield of conducting material is integrated onto the probe, the shield being partly covered by an insulating layer. The part of the shield not covered by the insulating layer, viz. the exposed part of the shield, provides a return electrode for a stimulating current path. The shield may cover most of the length of the probe and thus protect an enclosed wire extending from the one or more electrodes at the distal end of the probe to the proximal end of the probe against external electromagnetic fields, such as external RF fields. Thus, the shield with a layer of insulating material on a part thereof adjacent to at least one of the one or more electrodes, solves both problems regarding RF safety and a return path of stimulation current.

The term "a shield extending from the vicinity of an electrode" is meant to denote that the shield is close to or borders on the electrode, but that the electrode itself is not covered by the shield, or at least not covered entirely by the shield.

According to an aspect of the probe, the one or more electrodes of the probe are arranged at the distal end of the probe and the shield extends from the vicinity of at least one of the one or more electrodes towards the proximal end of the probe. Such an arrangement of electrodes at the distal end of the probe is particularly advantageous in the case where the probe is a part of a brain stimulator.

The term "electrodes at the distal end" is meant to denote that the electrodes are situated close to the distal end, in contrast to being placed in the proximal end or in an intermediary position between the distal and proximal ends, and that some electrodes may be situated at the very end of the probe whilst others are grouped around the distal end of the probe, contiguous to or bordering to neighboring electrodes.

According to other aspects of the probe, the one or more electrodes are arranged at a position between the distal end and the proximal end of the probe. The shield extends from the vicinity of at least one of the one or more electrodes towards the distal end of the probe, or the probe comprises two shields, whereof one shield extends from the vicinity of at least one of the one or more electrodes towards the distal end of the probe and the other of the two shields extends from the vicinity of at least one of the one or more electrodes towards the proximal end of the probe. Such a probe having electrodes arranged at an intermediary position between the proximal and distal ends of the probe, is in particular advantageous as a probe for a muscle-stimulator or a gastro-electrical stimulator.

According to an aspect of probe, the exposed area of the shield not covered by the layer of insulating material is at least one order of magnitude larger than the area of an individual electrode amongst the one or more electrodes. Hereby, the return electrode created by the exposed area of the shield is large compared to the one or more electrodes individually;

this ensures that the current density at the return electrode does not elicit unwanted stimulation effects.

According to another aspect of probe, the capacitive impedance of the insulating material is sufficiently high at low frequencies to substantially block any current flow. The term "low frequencies" is a well-defined term denoting frequencies below 300 kHz. Typically, neuro-stimulation pulses contain frequencies in the range from 0.001 to 10 kHz. Thus, the insulating material is arranged for blocking current flow induced by neuro-stimulation frequencies. Hereby, the exposed part of the shield of conducting material will function as a return electrode for stimulation current, whilst the insulating material ensures an insulation between the one or more electrodes at the distal end of the probe and the return electrode, so as to avoid short-cutting effects.

According to another aspect of the probe, the impedance of the insulating material is sufficiently low at high frequencies to become substantially transparent. The term "high frequencies" is a well-defined term denoting frequencies above 30 MHz. Typical MR frequencies are in the range from 64 to 128 MHz, viz. very high frequencies. Thus, the insulating material is substantially transparent to MR frequencies, which means that the current distribution at these MR frequencies is not changed by the insulating material. Thus, the insulating material does not influence the current distribution at MR frequencies, and the insulating material does not inhibit the shielding effect of the shield of conductive material. Therefore, the shielding effect of the shield of conductive material is effective along the entire extension of the shield of conductive material, not just at the exposed part thereof.

According to yet another aspect of the probe, the conducting material and the insulating material are biocompatible materials. For example, the insulating material may be one of the following materials or a combination thereof: paralyene, silicone, polyimide, polyureathene.

According to yet another aspect of the probe, the distal end of the probe comprises a plurality of electrodes and wherein the area of the shield not covered by insulating material is larger than the area of the sum of the areas of the electrodes in said plurality. Hereby, it is ensured that even when the probe comprises a plurality of electrodes, the return electrode is sufficiently large to avoid unwanted stimulation effects in the vicinity of the return electrode. Advantageously, the area of the shield not covered by insulation material may be at least twice the area of the sum of the areas of the electrodes in the plurality of electrodes.

According to a further aspect, the probe is part of a brain stimulation device, spinal cord stimulation device; pacemaker, cortical stimulation device, or muscle stimulation device.

According to yet a further aspect, an implantable electro-stimulation device comprising a probe according to any of the above aspects is provided.

The different aspects of the present invention may each be combined with any of the other aspects. These and other aspects of the invention will be apparent from and elucidated with reference to the embodiments described hereinafter.

BRIEF DESCRIPTION OF THE FIGURES

The present invention will now be explained, by way of example only, with reference to the accompanying Figures, where.

DETAILED DESCRIPTION OF AN EMBODIMENT

Figure 1:
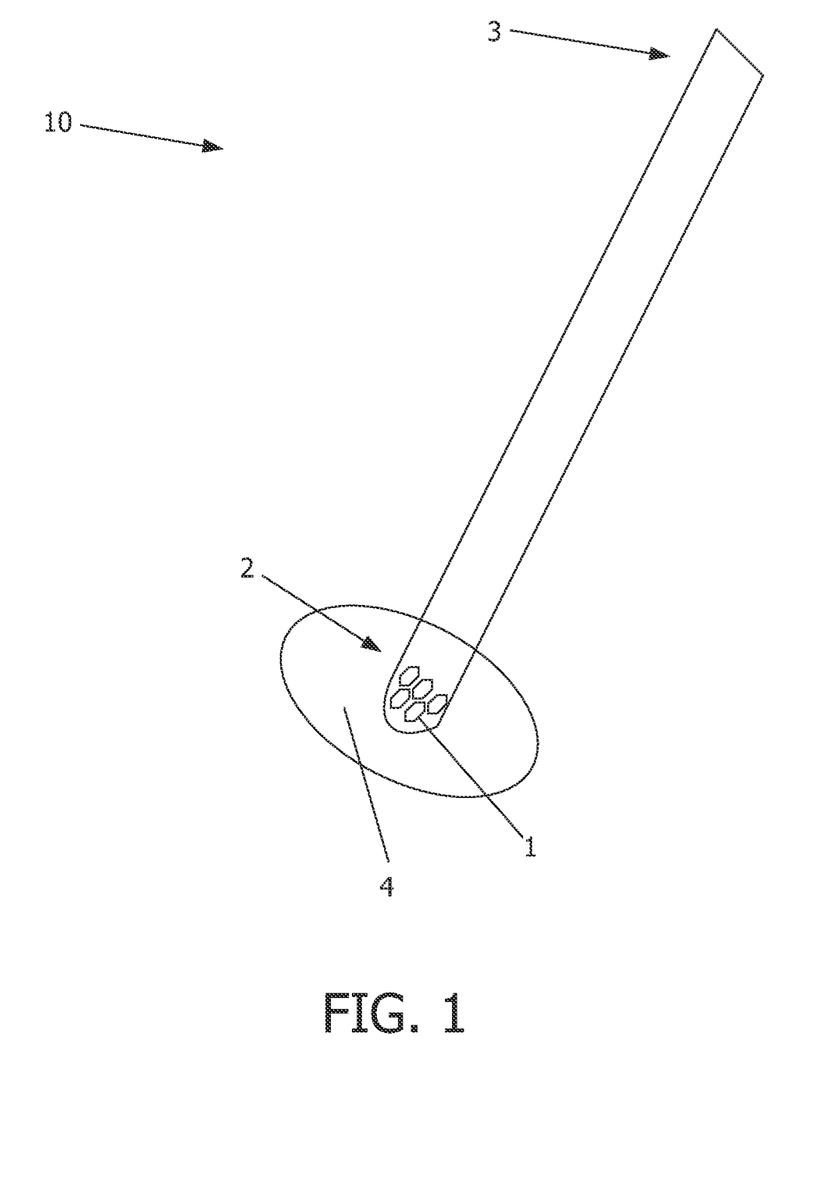
FIG. 1 shows the probe of an electro-stimulation device.

FIG. 1 shows the probe 10 of an electro-stimulation device. The probe 10 has a distal end 2 and a proximal end 3. The probe 10 has a plurality of electrodes 1 situated close to the distal 2 end thereof. Alternatively, only one electrode 1 would be conceivable; however in order to provide high resolution stimulation, more than one electrode is advantageous.

The probe is arranged for being implanted into the tissue of a patient to be treated, such as in the spinal cord, nerve roots, muscles, or brain tissue, in order to provide electrical stimulation of such a region of interest, the stimulation of which is expected to alleviate a condition of the patient. The electro-stimulation device typically comprises a battery (not shown) and a pulse generator (not shown) connected to the proximal end 3 of the probe 10 for generation of patterns of electric pulses that stimulate the tissue, via the electrodes 1 of the probe 10.

The reference numeral 4 denotes a volume of tissue surrounding the distal end of the probe. The volume 4 is meant to designate the volume of tissue that may be addressed by electro-stimulation by means of the electrodes 1 of the probe 10, when the probe 10 is implanted in the tissue of a patient.

Figure 2:
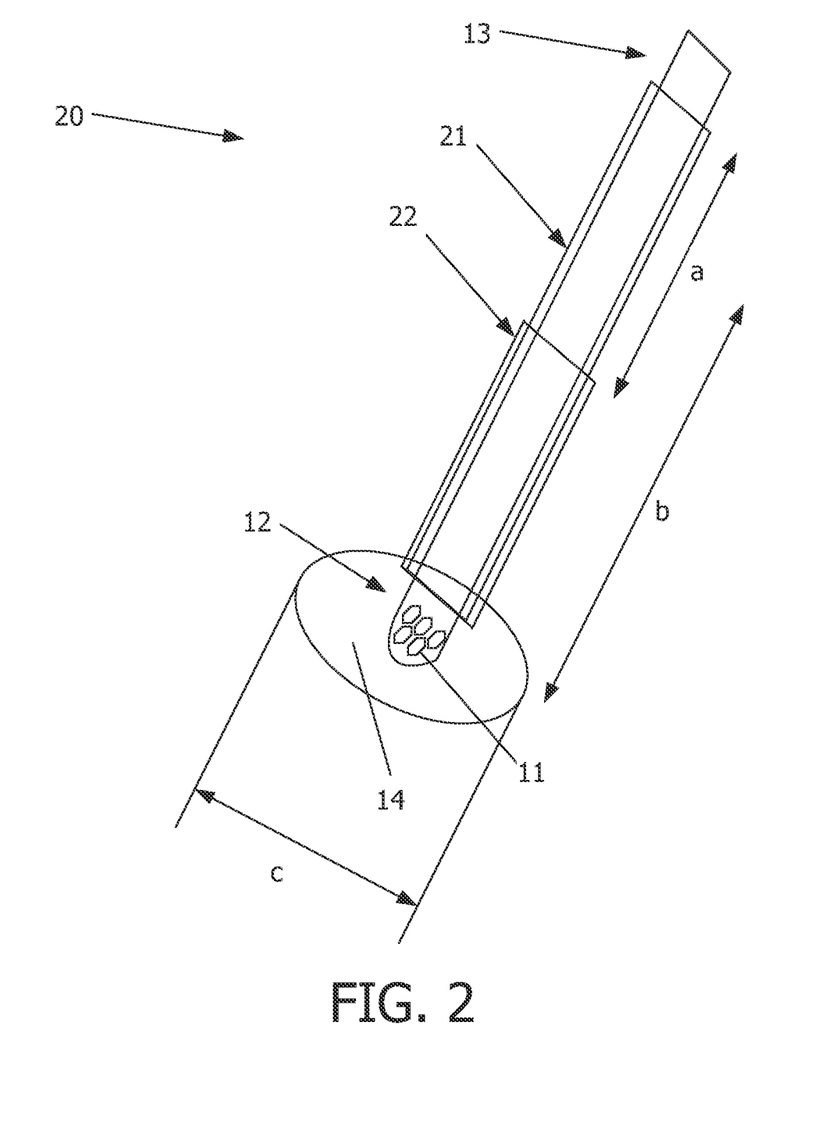
FIG. 2 shows the probe of an electro-stimulation device according to an embodiment of the invention.

In the probe of the electro-stimulation device shown in FIGS. 1 and 2, the electrodes are at the distal end of the probe. However, the electrodes might also be placed elsewhere, such as in the middle portion of the probe, depending on the direction at which the probe is arranged for insertion into the tissue and/or the type of device with which the probe is used. For example muscle stimulator devices or gastro-electrical stimulators may comprise probes having electrodes at an intermediary position between the distal and the proximal ends of the probe.

FIG. 2 shows the probe 20 of an electro-stimulation device according to an embodiment of the invention.

The probe 20 has a distal end 12 and a proximal end 13. The probe 20 has a plurality of electrodes 11 situated close to the distal 12 end thereof. Alternatively, only one electrode 11 would be conceivable; however in order to provide high resolution stimulation, more than one electrode is advantageous. The electrodes 11 are grouped together in opposition to being spread out along the length of the probe 10.

The probe 20 is arranged for being implanted into the tissue of a patient to be treated, such as in the spinal cord, nerve roots, muscles, or brain tissue, in order to provide electrical stimulation of such a region of interest, the stimulation of which is expected to alleviate a condition of the patient. The electro-stimulation device typically comprises a battery (not shown) and a pulse generator (not shown) connected to the proximal end 13 of the probe 20 for generation of patterns of electric pulses that stimulate the tissue, via the electrodes 11 of the probe 20.

The reference numeral 14 denotes a volume of tissue surrounding the distal end 12 of the probe 20. The volume 14 is meant to designate the volume of tissue that may be addressed by electro-stimulation by means of the electrodes 11 of the probe 20, when the probe 20 is implanted in the tissue of a patient.

The probe 20 moreover comprises a combined return electrode and RF shield, in that the probe 20 comprises a shield of conductive material 21 extending along most of the length of the probe 20. The shield 21 advantageous extends from a position close to the electrodes 11 to a position close to the proximal 13 end of the probe 20 in order to shield most of the length of any wire (not shown) from an electrode 11 to the proximal end 13 of the probe 20 against external signals.

A part of the shield 21 is embedded under or covered by a layer of insulating material 22. The part of the shield 21 not covered by insulating material is denoted "a" in FIG. 2. This exposed part a of the shield constitutes a return electrode for current from the stimulation electrodes 11 during electro-stimulation.

Advantageously, the distance b between the array of electrodes 1 and the return-electrode is larger than the size c of the tissue volume 14 to be addressed. Hereby, it is ensured that stimulation current is sufficiently spread into the tissue volume 14 to be stimulated. Moreover, the surface area of the exposed return electrode a is advantageously much larger than the size of the individual stimulation electrodes 11. Hereby, the current density at the return electrode a does not elicit unwanted stimulation effects.

The distance b in FIG. 2 is meant to denote the distance between the center of the tissue volume 14 addressed in electro-stimulation and the midpoint or middle of the exposed return electrode a.

Figure 3A:
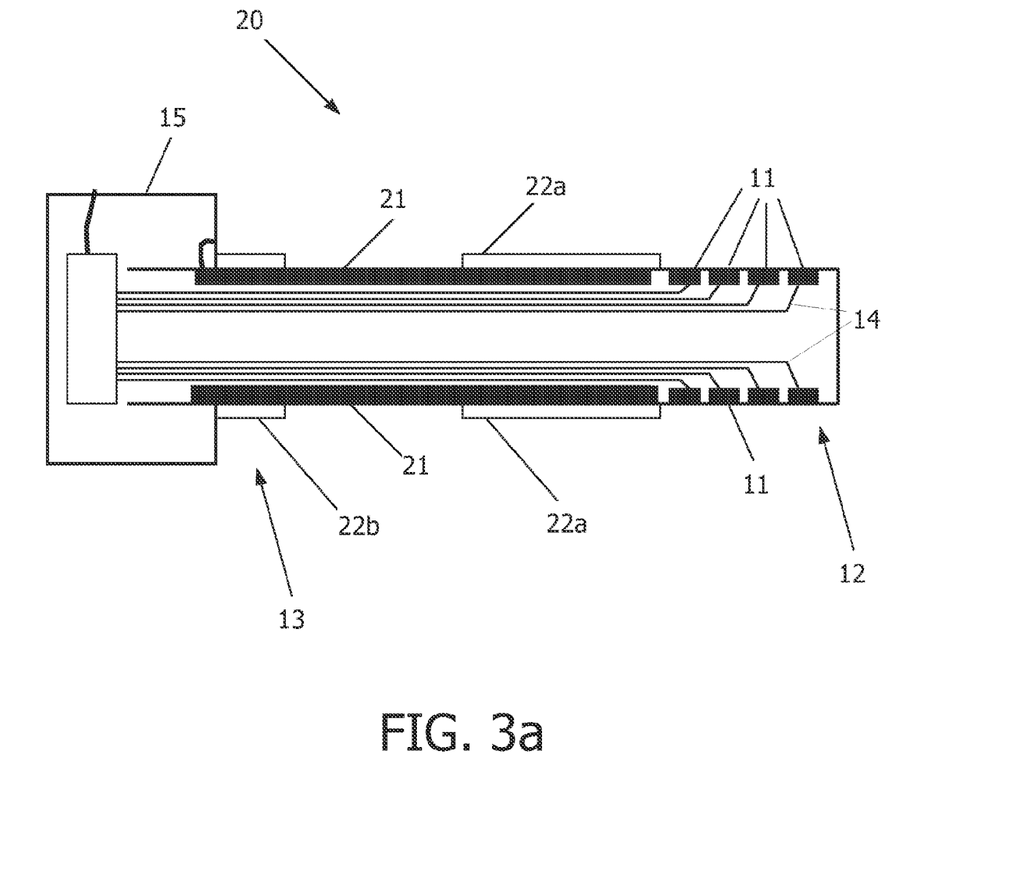
FIGS. 3a and 3b are cross sectional view of electro-stimulation probes according to two embodiments of the invention.
Figure 3B:
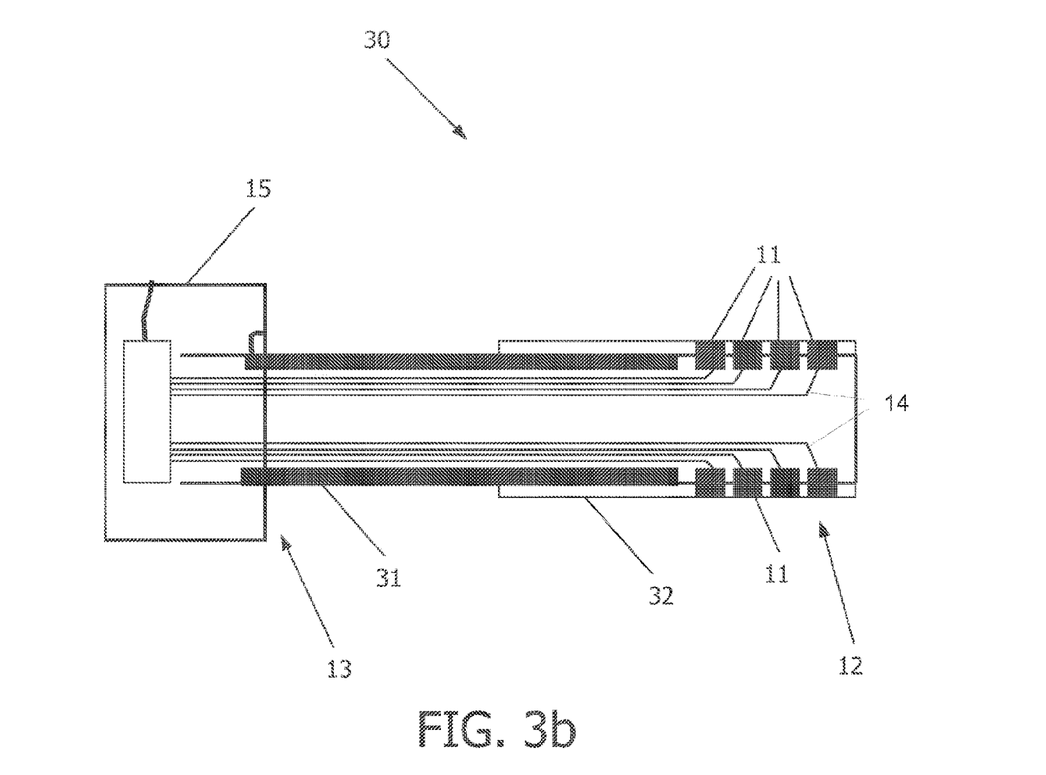

From FIG. 2 it is clear that the shield 21 extends from close to the distal end 12 of the probe 20 to close to the proximal end 12 of the probe 20, and that the layer of insulating material 22 covers a part of the shield 21, viz. the part of the shield 21 being closest to the distal end 12 of the probe 20. As shown in FIGS. 3a and 3b, the insulating layer 22 may extend further towards the distal end 12 of the probe 20 than the shield 21 of conductive material. The probe 20, the shield 21 and the insulating layer 22 may be cylindrical. The shield 21 and the insulating material 22 advantageously extend all along the radial circumference of the probe.

The number of electrodes 11 may be any appropriate number equal to or larger than one. Even though only five electrodes are disclosed in FIG. 2, a higher number of electrodes may be advantageous in order to provide high resolution stimulation. An example of a high resolution probe is a probe with 64 electrodes at the distal end of the probe.

The term "electrodes at the distal end" is meant to denote that the electrodes are situated close to the distal end, in contrast to being placed in the proximal end or in an intermediary position between the distal and proximal ends, and that some electrodes may be situated at the very end of the probe whilst others are grouped around the distal end of the probe.

The probe 20 is typical a cylindrical probe having a diameter of e.g. 1.2 mm. The surface area of a single electrode 11 may be in the order of 0.4 mm$^2$, and the total area of the combined array of the one or more electrodes including the space between the electrodes, may take up 15 mm of the length of the probe 20, corresponding to a total electrode area of around 20 mm$^2$. The length of the probe 20 may for example be around 10 cm. The distance between the electrode which is the closest to the exposed part of the shield and the exposed part of the shields is typically at least 10 mm.

FIG. 3a is a cross sectional view of an electro-stimulation probe 20 according to an embodiment of the invention. The probe 20 has a distal end 12 and a proximal end 13. The probe 20 has a plurality of electrodes 11 situated close to the distal 12 end thereof. Alternatively, only one electrode 11 would be conceivable; however in order to provide high resolution stimulation, more than one electrode is advantageous. FIG. 3a moreover illustrates a chamber 15 housing electronics connected to the proximal end 13 of the probe 20 and wires 14 extending from each of the electrodes 11 to the proximal end 13 of the probe 20 and to the chamber 15.

Embedded within or integrated in the outer surface of the probe 20 is a shield 21 of conductive material. The shield extends along the length of the probe 20, from the proximal end 13 towards the distal end 12 of the probe 20. The edge of the shield 20 facing towards the electrodes 11 is relatively close to the most proximal electrodes. The shield 21 protects the signal wires 14 from external electromagnetic fields.

A part of the shield 21 is covered by a layer 22a of insulating material extending along the length of the probe 20. The layer 22a extends further along the length of the probe 20 towards the electrodes 11 than the shield 21. An auxiliary, separate layer of insulating material 22b may be provided close to the chamber 15 in order to isolate the return electrode from the chamber 15. The insulating layers 22a, 22b block part of the large shield 21 in order to preserve the current return path as desired during neuro-stimulation.

FIG. 3b is a cross sectional view of an alternative electro-stimulation probe 30 according to an embodiment of the invention. The probe 30 has a distal end 12 and a proximal end 13. The probe 30 has a plurality of electrodes 11 situated close to the distal end 12 thereof. Again, only one electrode 11 could be conceivable; however in order to provide high resolution stimulation, more than one electrode is advantageous. FIG. 3b also illustrates a chamber 15 housing electronics connected to the proximal end 13 of the probe 30 and wires 14 extending from each of the electrodes 11 to the proximal end 13 of the probe 30 and to the chamber 15.

Embedded within or integrated in the outer surface of the probe 30 is a shield 31 of conductive material. The shield extends along the length of the probe 30, from the proximal end 13 towards the distal end 12 of the probe 30. The edge of the shield 30 facing towards the electrodes 11 is relatively close to the most proximal electrodes. The shield 31 protects the signal wires 14 from external electromagnetic fields.

A part of the shield 31 is covered by a layer 32 of insulating material extending along the length of the probe 20. The layer 32 extends all along the length of the probe 30 to the distal end 12 thereof. The insulating layer 32 blocks part of the large shield 21 in order to preserve the current return path as desired during neuro-stimulation.

The shield of conductive material of the probes 20, 30 illustrated in FIGS. 2, 3a and 3b provides a protection of the enclosed wires (14 in FIGS. 3a and 3b) from external RF fields. Since the shield covers most of the length of the probes 20, 30, most of the length of the wires is protected by the shield. The exposed part of the shield serves as a return electrode for stimulating current path.

The conflicting requirements regarding to the distance from the stimulating electrodes are reconciled by adding an insulating layer that partially blocks the return electrode at neuro-stimulation frequencies, typically lower than 10 kHz, but that is relatively transparent at MR frequencies, viz. typically 64-128 MHz. Thus, the layer of insulating material does not change the current distributions at MRI frequencies, but blocks the low-frequency stimulating currents. The layer of insulating material partially covering the shield thus implements a frequency differentiator. For stimulation frequencies, the insulation layer has a very high impedance and only the exposed part of the shield not covered by the insulating material acts as a return electrode. For MR frequencies, the capacitance of the capacitor formed by the insulating material and the tissue and shield is high enough to form a very low or negligible impedance, so that the insulating material will be substantially transparent to MR frequencies.

Figure 4:
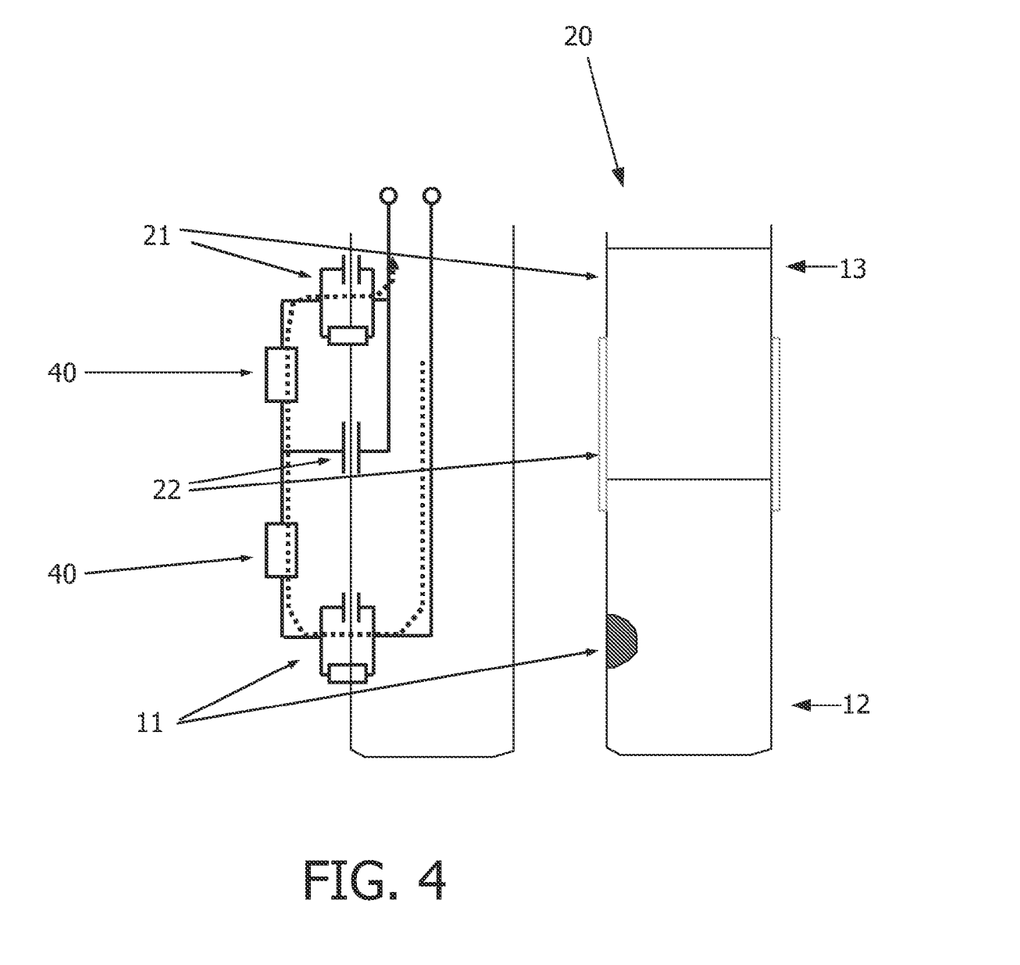
FIG. 4 is an equivalent circuit model of a probe according to an embodiment of the invention.

FIG. 4 is an equivalent circuit model of a probe 20 according to an embodiment of the invention. On the left hand side of FIG. 4 is shown the equivalent circuit of the probe 20, and on the right hand side is shown the corresponding probe 20. The probe has a proximal end 13 and a distal end 12, and an electrode 11 is shown at the distal end 12 of the probe. Also shown is the insulating layer 22 and the shield 21 of conductive material.

The equivalent circuit diagram shows the resistance 40 constituted by tissue into which the probe 20 is implanted as well as the capacitances between the electrode 11, the insulating layer 22 and the return electrode part of the shield 21. The path of neurostimulation current is illustrated by the broken line.

EXAMPLE

Numeral values of the impedance of a probe are given in the following, only as an example. These values are thus not to be taken as limiting the invention.

In general, the capacitive impedance of the insulating layer needs to be high enough at neuro-stimulation frequencies, typically 0.001-10 kHz, to effectively block the current flow. On the other hand, the impedance of the insulating layer should be low enough at MR frequencies, typically 64-128 MHz, so that the insulating layer becomes relatively transparent. Thus the induced current can spread across the entire shield instead of accumulating at some parts.

The capacitance of two concentric cylindrical shells of length L and respective radii $r_1$ and $r_2$ is given by $$C = \frac{2\pi\varepsilon_0\varepsilon_r L}{\ln(r_2/r_1)}$$

Therefore, the impedance of a cylindrical layer with diameter d and thickness t for a signal with frequency f is given by $$Z = \frac{1}{2\pi fC} = \frac{\ln(1 + 2t/d)}{4\pi^2 \varepsilon_0 \varepsilon_r L}$$

Calculations of this impedance using typical values in a DBS probe are presented in Table 1.

TABLE 1

| Neuro-stimulation frequency | f_STIM | 1000 | Hz |
| --- | --- | --- | --- |
| MR frequency | f_MR | 6.40E+07 | Hz |
| Electric constant | $\varepsilon_0$ | 8.90E−12 | F/m |
| Insulating layer permittivity | $\varepsilon_r$ | 3 | |
| Probe diameter | d | 1.27E−03 | m |
| Length of insulating layer | L | 2.00E−02 | m |

| Calculated layer capacitive impedance: | | |
| --- | --- | --- |
| Insulating layer thickness t (m) | Zstim (ohm) | Zmr (ohm) |
| 1.00E−07 | 7.51E+03 | 1.17E−01 |
| 1.00E−06 | 7.51E+04 | 1.17E+00 |
| 1.00E−05 | 7.51E+05 | 1.17E+01 |

As shown in Table 1, a 1 μm thick insulating layer has an impedance of 75 kOhm at 1 kHz, which is a typical neuro-stimulation frequency. At this neuro-stimulation frequency, the tissue impedance is lower than 1 kOhm and the return electrode is so large that its impedance is negligible. Hereby, the impedance of the insulating layer is high enough to block the neuro-stimulation signal current flow. At MR frequencies, the impedance is indeed very low, viz. 1.17 Ohm, so that the insulating layer becomes transparent.

Biocompatible conductive materials with sufficient mechanical strength, such as Pt/Ir, could advantageously be used for the large return electrode. The insulating layer can be made of biocompatible polymers such as parylene, silicone, polyimide, polyurathene, or a combination of them.

In short, the invention relates to a probe for an implantable electro-stimulation device. The probe has a distal end and a proximal end, and moreover comprises: one or more electrodes at the distal end of the probe; a shield of conducting material covering a major part of the probe, said shield extending from the vicinity of at least one of the one or more electrodes towards the proximal end of the probe; and a layer of insulating material covering part of the shield in the vicinity of the at least one of the one or more electrodes. The shield protects wires, extending from electrodes to the proximal end of the probe, from undesired interference of external RF fields. The exposed part of the shield not covered by the layer of insulating material serves as a return electrode for the neurostimulation signal path.

Although the present invention has been described in connection with the specified embodiments, it is not intended to be limited to the specific form set forth herein. Rather, the scope of the present invention is limited only by the accompanying claims. In the claims, the term "comprising" does not exclude the presence of other elements or steps. Additionally, although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

The invention claimed is:

1. A probe for an implantable electro-stimulation device, said probe comprising:
   a distal end and a proximal end;
   one or more electrodes on the probe;
   a shield of conducting material covering a part of the probe, said shield extending from the vicinity of the one or more electrodes towards the proximal end or towards the distal end of the probe; and
   a layer of insulating material covering part of the shield in the vicinity of the one or more electrodes,
   wherein an exposed area of the shield not covered by the layer of insulating material is at least one order of magnitude larger than an area of one of the one or more electrodes, and is configured to be a return electrode for electrical stimulation current from the electrodes, and wherein at least a portion of the layer of insulating material covering the part of the shield is between the one or more electrodes and the exposed area of the shield.

2. A probe according to claim 1, wherein the one or more electrodes are arranged at the distal end of the probe and the shield extends from the vicinity of at least one of the one or more electrodes towards the proximal end of the probe.

3. A probe according to claim 1, wherein the one or more electrodes are arranged at a position between the distal end and the proximal end of the probe, and wherein the shield extends from the vicinity of at least one of the one or more electrodes towards the distal end of the probe.

4. A probe according to claim 1, wherein the one or more electrodes are arranged at a position between the distal end and the proximal end of the probe, and wherein the probe comprises two shields, wherein one of the two shields extends from the vicinity of at least one of the one or more electrodes towards the distal end of the probe and the other of the two shields extends from the vicinity of at least one of the one or more electrodes towards the proximal end of the probe.

5. A probe according to claim 1, wherein a capacitive impedance of the insulating material is sufficiently high at frequencies between 0.001 Kilohertz (kHz) and 10 kHz to substantially block any current flow.

6. A probe according to claim 1, wherein a capacitive impedance of the insulating material is sufficiently low at frequencies above 30 Megahertz to become substantially transparent to allow an induced current to spread across the shield.

7. A probe according to claim 1, wherein the conducting material and the insulating material are biocompatible materials.

8. A probe according to claim 1, wherein the insulating material is one or more of parylene, silicone, polyimide, or polyurethane.

9. A probe according to claim 1, wherein the distal end of the probe comprises a plurality of the one or more electrodes and wherein an area of the shield not covered by insulating material is larger than an area comprising a sum of each area of the plurality of the one or more electrodes.

10. A probe according to claim 1, wherein the implantable electro-stimulation device is part of a brain stimulation device, spinal cord stimulation device pacemaker, cortical stimulation device, or muscle stimulation device.

11. A probe according to claim 1, wherein the exposed area of the shield extends continuously from the proximal end of the probe to a proximal end of the layer of insulating material.

12. A probe according to claim 1, wherein a capacitive impedance of the insulating material is sufficiently high at frequencies below 300 KHz to substantially block any current flow,
wherein the capacitive impedance of the insulating material is configured such that the insulating layer blocks flow of stimulation current to the covered part of the shield at neuro-stimulation frequencies being lower than 10 kHz, and
wherein the capacitive impedance of the insulating material is sufficiently low at magnetic resonance (MR) frequencies between 64-128 MHz to become substantially transparent to allow an induced current to spread across the shield.

13. A probe according to claim 1 wherein the insulating material is parylene.

14. A probe according to claim 1 wherein the insulating material is polyimide.

15. A probe according to claim 1, wherein the layer of insulating material in the vicinity of the at least one of the one or more electrodes is configured to block part of the shield to preserve a current return path via the return electrode during delivery of the electrical stimulation current.

16. A probe according to claim 1, wherein the conducting material of the shield includes platinum-iridium alloy.

17. A probe according to claim 1, further comprising a second layer of insulating material covering part of the shield in the vicinity of the proximal end of the probe, wherein the second layer of insulating material is configured to block part of the shield from a chamber of the implantable electro-stimulation device to preserve a current return path via the return electrode during delivery of the electrical stimulation current.

18. A probe according to claim 1, wherein at least one of the one or more electrodes and the shield are configured to form an electrical circuit when the probe is implanted within tissue of a patient.

19. A probe according to claim 1, wherein the portion of the shield covered by the layer of insulating material in the vicinity of the at least one of the one or more electrodes blocks a first part of the shield to preserve a current return path via the return electrode during delivery of the electrical stimulation current, the probe further comprising a second layer of insulating material covering part of the shield in the vicinity of the proximal end, wherein the second layer of insulating material blocks a second part of the shield from a chamber of the implantable electro-stimulation device to preserve the current return path via the return electrode during delivery of the electrical stimulation current.

20. An implantable electro-stimulation device comprising:
a probe, wherein the probe comprises:
a distal end and a proximal end;
one or more electrodes located on the probe distal to the proximal end;
a shield of conducting material covering a part of the probe, said shield extending from the vicinity of the one or more electrodes towards the proximal end or towards the distal end of the probe; and
a layer of insulating material covering part of the shield in the vicinity of the one or more electrodes,
wherein an exposed area of the shield not covered by the layer of insulating material is at least one order of magnitude larger than an area of one of the one or more electrodes, and is configured to be a return electrode for electrical stimulation current from the electrodes, and wherein at least a portion of the layer of insulating material covering the part of the shield is between the one or more electrodes and the exposed area of the shield; and
a pulse generator configured to generate electric pulses to stimulate tissue of a patient via the electrodes of the probe, wherein the shield is configured to shield a portion of wires extending from the electrodes to the proximal end of the probe from an external electromagnetic field.

21. An implantable electro-stimulation device according to claim 20, wherein a capacitive impedance of the insulating material is sufficiently low at frequencies above 30 Megahertz to become substantially transparent to allow an induced current to spread across the shield.

22. An implantable electro-stimulation device according to claim 20, wherein a capacitive impedance of the insulating material is sufficiently high at frequencies between 0.001 Kilohertz (kHz) and 10 kHz to substantially block any current flow.

23. An implantable electro-stimulation device according to claim 20, wherein at least one of the one or more electrodes and the shield of the probe are configured to form an electrical circuit when the probe is implanted within tissue of a patient.

24. An implantable electro-stimulation device according to claim 20, wherein the portion of the shield covered by the layer of insulating material in the vicinity of the at least one of the one or more electrodes blocks a first part of the shield to preserve a current return path via the return electrode during delivery of the electrical stimulation current, wherein the probe further comprises a second layer of insulating material covering part of the shield in the vicinity of the proximal end, and wherein the second layer of insulating material blocks a second part of the shield from a chamber of the implantable electro-stimulation device to preserve the current return path via the return electrode during delivery of the electrical stimulation current.

\* \* \* \* \*